United States Patent [19]

Geffard

[11] Patent Number: 4,762,781

[45] Date of Patent: Aug. 9, 1988

[54] ANTIBODIES CAPABLE OF SPECIFICALLY IDENTIFYING HAPTENIC GROUPS, THEIR PREPARATION AND THEIR USE AND TO NEW ANTIGENS PERMITTING THEIR PREPARATION

[75] Inventor: Michel Geffard, Merignac, France

[73] Assignees: Centre National de la Recherche Scientifique (CNRS); Institut National de la Sante et de la Recherche Medicale (INSERM), both of Paris, France

[21] Appl. No.: 687,033

[22] Filed: Dec. 28, 1984

[30] Foreign Application Priority Data

Dec. 30, 1983 [FR] France .................... 83 21087

[51] Int. Cl.$^4$ ............... G01N 33/531; G01N 33/532; G01N 33/543
[52] U.S. Cl. ........................ 435/7; 435/188; 436/503; 436/578; 436/543; 436/547; 436/815; 436/822; 530/387; 530/391; 530/807
[58] Field of Search ............... 436/532, 543, 815, 816, 436/817, 822, 823, 547, 503; 435/7, 188; 530/391, 387, 807

[56] References Cited

U.S. PATENT DOCUMENTS 4,410,634 10/1983 Cooper et al. ................. 436/543
4,511,550 4/1985 Yokoyama et al. .............. 424/1.1

OTHER PUBLICATIONS

F. E. Bloom et al, *Pharmacological Reviews* 25, 343–358, 1973.

Y. Weinstein et al, *Journ. Clin. Invest.* 52, 1349–1361, 1973.

J. D. Roberts et al, *Basic Principles of Organic Chemistry*, W. A. Benjamin, Inc., New York, 1964, p. 650.

E. A. Kabat, *Structural Concepts in Immunology and Immunochemistry*, Holt, Rinehart and Winston, Inc., New York, 1968, p. 89.

*Primary Examiner*—Robert J. Warden
*Assistant Examiner*—David A. Saunders
*Attorney, Agent, or Firm*—Cushman, Darby & Cushman

[57] ABSTRACT

New antibodies capable of specifically identifying hapten groups, characterized by the fact that said hapten groups correspond to the formula:

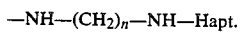

in which n is a whole number between 4 and 6, and Hapt. is the residue of the hapten molecule of formula Hapt.—NH$_2$ (—NH$_2$ being a primary amine group) or of formula Hapt.=NH (=NH being the imine of a guanidine type group);

their preparation through immunization using immunogens of the formula:

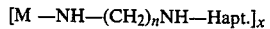

and their application, particularly in visualizing and determining the quantity of haptens.

17 Claims, No Drawings

ANTIBODIES CAPABLE OF SPECIFICALLY IDENTIFYING HAPTENIC GROUPS, THEIR PREPARATION AND THEIR USE AND TO NEW ANTIGENS PERMITTING THEIR PREPARATION

The present invention concerns new antibodies capable of specifically identifying hapten groups, the preparation and application of said antibodies, and new antigens for use in preparing them.

It is known that many small molecules are not able to induce antibody production alone, although they are able to react with antibodies. These molecules are called haptens. In order to induce the production of antibodies targeted against the haptens, it is first necessary to fix the hapten, generally covalently, to a larger molecule called a carrier. The substance obtained (said to be "conjugated") is then able to stimulate the production of antibodies and constitutes an immunogen.

Likewise it is known that because of their great sensitivity, antigen-antibody reactions constitute a particularly useful method of detecting, proportioning, and visualizing haptens, particularly through immunofluorescent techniques and radioimmunoassays. These methods have already been used for such purposes as the quantification of various hormones.

In the field of neurobiology, it is known that being able to specifically identify informative molecules, and to localize them in the central nervous system, presently constitutes one of the most important subjects of research, since it allows us to study not only the organization but the functioning of the central nervous system. There is no doubt but that this research will make possible a better understanding of various phenomena such as sleep, memory, smell, etc., and will thus enable us to invent new diagnostic methods and new therapeutic means to be applied to various disorders of the nervous system. However, the relations between the neuroeffector substances and the structure of the central nervous system are very difficult to study, and research on them proceeds slowly.

Immunologic methods appear to be especially promising in this area. Here, too, however, progress has been relatively slow since the first tests of obtaining antibodies targeted against indole derivatives were described by Ranadive, N. S., and Sehon, A. H., *Can. J. Biochem.* 45, pp. 1689–1700 (1967).

In order to be able to put these immunologic methods to use, the first problem to be solved is that of obtaining an immunogen that will induce the production of highly specific and closely related antibodies. We know that by administering a hapten coupled with a carrier (protein), we generally obtain three large categories of antibodies, i.e., those that are targeted against the carrier, those that are targeted against the hapten, and those that are targeted against an antigen determinant situated in the zone of contact between the hapten and the carrier. Generally, the anticarrier antibodies are eliminated over a solid immunoadsorbant containing the hapten. Only the specific antibodies become fixed and can then be eluted.

It is thus easy to imagine that the nature of the coupling between the hapten and the carrier is likely to play a very important role in obtaining antibodies that are highly specific against the hapten.

The coupling of certain indolamines by succinylation was recently suggested (M. R. Geffard, et al., *J. Neurochem.* 39, pp. 1271–1277, (1982).

We have now discovered that it is possible to obtain highly specific anti-hapten antibodies using an immunogen obtained by coupling hapten with certain dialdehydes, following the reaction with a reduction of the neoformed imine bonds. It is generally possible in this way to obtain antibodies that will be sufficiently specific to obviate the need for passing the immune serum over an immunoadsorbant containing hapten.

The degree of specificity of the antibodies obtained can be checked by testing them using marked antigens obtained in the same manner as the immunogen, by coupling the hapten in question, or haptens of a similar chemical structure, with a molecule of low molecular weight possessing an amine group, which may be a lysine derivative, using the same dialdehyde. The coupling may be followed, as previously, with reduction of the imine groups.

The present invention concerns new antibodies capable of specifically identifying hapten groups, characterized by the fact that said hapten groups are described by formula I:

$$-NH-(CH_2)_n-NH-Hapt. \qquad (I)$$

in which n is a whole number between 4 and 6, and Hapt. is the residue of the hapten molecule of formula Hapt.—$NH_2$ (with —$NH_2$ here being a primary amine group) or Hapt.=NH (with =NH here being imine from a group of the guanidine type).

Examples of particular haptens that it is possible to identify using said antibodies are given below in the description of the process for preparing the antibodies.

The invention extends to said antibodies, modified by being marked with a fluorescent, enzyme, or radioactive tracer obtained using conventional methods for preparing such marked antibodies.

For example, the tracer may be a radioactive tracer obtained through isotope exchange using a radioactive isotope such as I 125. The coupling of the antibodies with a radioactive tracer agent is in itself known and may be performed using Greenwood's method.

The coupling of antibodies with a fluorochrome (e.g., isothiocyanate of fluorescein or rhodamine) is well known.

The coupling of antibodies with an enzyme tracer is also known in itself and may be performed using a method analogous to that described by Nakane, *Journal Histochemistry Cytochemistry*, 22: 1984–1991 (1974), which consists of fixing the enzyme onto immunoglobulin molecules.

The enzyme may be a peroxide or an alkaline phosphatase.

The enzymatic activity that may be present in the reagent after a test may be determined in accordance with known methods using an appropriate substrate that will enable revelation by colorimetry, fluorescence, luminescence, potentiometry, etc.

The invention also extends to monoclonal antibodies obtained using the known technique of hybridomes, starting from lymphocytes taken from animals immunized in accordance with the method that will be described hereinafter.

The invention further extends to polyclonal or monoclonal antibodies, marked or unmarked, that are fixed to a solid backing which makes it possible to use them as immunoadsorbant agents in chromatographic processes or as analytic reagents.

The backing may be made from any solid substance, biological or synthetic, that is endowed with adsorbant properties or is capable of fixing a coupling agent. These substances are known and described in the literature. Among the solid substances that are capable of fixing antibodies by adsorption are polystyrene, polypropylene, latexes, etc. Among the substances that may be used to fix antibodies by covalence using a coupling agent are dextran, cellulose, and their amine derivatives (diethylamino-cellulose or diethylamino-dextran).

The backing may be in the form of disks, tubes, rods, balls, or microtitration plates.

The coupling agents that make it possible to fix the antibodies onto the solid backing by covalence are bifunctional derivatives such as dialdehydes, quinones, etc.

The antibodies may also be fixed on solid mineral backings, for example using the methods described in French Pat. Nos. 76.23.176, 77.28.161, and 77.28.163.

The invention also concerns a process for preparing antibodies as defined above.

This process is characterized principally by the fact that, using known methods, animals are immunized through repeated adminstrations of one or more immunogens of formula II:

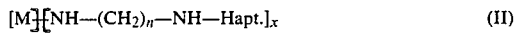   (II)

with M being the residue of an aminated macromolecule of the formula:

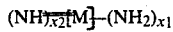

in which —$NH_2$ is a primary amine group and =NH is the imine of a group of the guanidine type, with Hapt. being the residue of the hapten molecule having the formula Hapt.—$NH_2$ or Hapt.=NH, the —$NH_2$ group being a primary amine group, =NH the imine of a group of the guanidine type, n a whole number between 4 and 6, $x_1$ a number equal to or greater than 1 and at most equal to the number of primary —$NH_2$ amine groups carried by said aminated macromolecule, and $x_2$ zero or a number no greater than the number of guanidine type groups carried by said aminated macromolecule (with $x_1+x_2=x$). The process is further characterized by the fact that the seral antibodies of said immunized animals are collected and, if necessary, fixed upon a backing according to known methods and/or caused to react with a radioactive, fluorescent, or enzyme marker using known methods. Conventional fractioning techniques enabling immunoglobulins to be isolated are used to collect the seral antibodies.

In preferred embodiments, the process for preparing antibodies under the invention may further have the following characteristics, taken separately or in combination:

said hapten is a compound taken from among the hormones, amine acids, oligopeptides, vitamins, drugs, toxins, neuromodulators, and neuromediators, or from the precursors or analogues of these compounds;

said hapten is a catecholamine or a precursor of catecholamine;

said hapten is taken from among phenylalanine, dihydroxyphenylalanine (DOPA), dopamine, norepinephrine, and epinephrine;

said hapten is taken from among tyramine and octopamine;

said hapten is an indolamine, which may be taken from among serotonin, 5-hydroxytryptophane, 5-methoxytryptophane, 5-methoxytryptamine, tryptophane, and tryptamine;

said hapten is an aminated acid or salt of said acids; the aminated acid possibly being taken from among glutamic acid, aspartic acid, taurine, and gamma-aminobutyric acid;

said hapten is an oligopeptide containing 2 to 5 amine acid figures;

said hapten is tetrodotoxin, saxitoxin, or their functional analogues derived from 2-imino hexahydropyrimidine;

said amine macromolecule has a molecular weight greater than 1,000;

said amine macromolecule contains lysine residues with a free $\epsilon$—$NH_2$ group;

generally, an antigen macromolecule is used, though this is not always necessary, particularly when giving booster shots during the process of immunizing the animals;

said amine macromolecule is a protein, a protein fragment, or a synthetic or semisynthetic polypeptide (polypeptidylprotein), or even a wall of bacterial cells from which the polysaccharide antigen determinants linked with lipid A, etc., may have been eliminated by hydrolysis; e.g., serum albumin, hemoglobin, polylysine, etc.

The invention also concerns the new antigens that are used with immunization to obtain the antibodies described above.

These antigens, consisting of a hapten having a primary amine group or a guanidine type group and linked to an amine molecule by means of a coupling agent, are characterized by the fact that they are described by formula III:

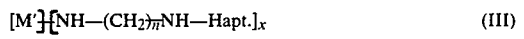   (III)

in which:

M' is the residue of an amine molecule of the formula:

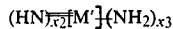

Hapt. is the residue of the hapten molecule of the formula Hapt.—$NH_2$ or Hapt.=NH, with the —$NH_2$ groups being imines of guanidine type groups, n is a whole number from 4 to 6, $x_3$ is a number, possibly zero, no greater than the number of primary amine groups —$NH_2$ carried by said amine molecule, and $x_2$ is zero or a number no greater than the number of guanidine type groups carried by said amine molecule (with $x_3+x_2=x$).

The invention also extends to said antigens, modified by being marked with a tracer, e.g., a radioactive tracer, and to said antigens fixed onto a solid backing using conventional fixing techniques, which may make use of bifunctional coupling agents.

When the amine molecule is a macromolecule (M'=M), the antigen can be used as an immunogen.

When the amine molecule is not a macromolecule, the antigen can be used to follow the development of the quantity of antibodies during immunization and to verify the specificity and affinity of the antibodies obtained after immunization. As indicated above, these antigens are prepared in the same way as the immunogens but using amine molecules M"—$NH_2$ (primary amine) or M''=NH (molecule with guanidine type group) with low molecular weight, generally less than 1,000, and most often less than 500, e.g., N-α-acetyl-L-lysine N-methylamide or tripeptide proline-phenylalanine-lysine. Said antigens of formula IV:

$$M'''-NH-(CH_2)_n-NH-Hapt. \quad (IV)$$

are also part of the invention. They are generally used in the form of antigens marked with a tracer, e.g., a radioactive tracer, for the purpose of studying antibodies using known methods, e.g., the method of equilibrium dialysis.

The invention also concerns a process for preparing an antigen as defined above.

This process is characterized chiefly by the fact that:
(a) a dialdehyde of formula $$O=CH-(CH_2)_{\overline{n-2}}CH=O$$

is caused to react in a solution of hapten and a solution of the amine molecule, and
(b) the product obtained, having formula V $$[Hapt.-Y-(CH_2)_{\overline{n-2}}CH=N^+\overline{_{x2}}[M']\{N=CH-(CH_2)_{\overline{n-2}}Y-Hapt.]_{x3}$$

in which $x_3$ and $x_2$ are defined as above, Y represents a —N=CH— group linked by nitrogen to the Hapt. residue after the hapten has reacted through its primary amine function, and Y represents a =N⊕=CH— group linked by nitrogen to the Hapt. residue after the hapten has reacted through its guanidine type group, is subjected to the action of a reducing agent capable of reducing imine groups or =N⊕=CH— groups into amine groups.

The reaction of aldehydes on primary amines, and the reduction into secondary amines of the imines obtained, are well known reactions in organic chemistry.

Similarly, the reaction of molecules with a group of the guanidine (or guanidinium) group on aldehydes is known. It takes place according to the following diagram:

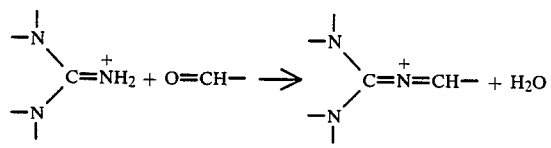

and the compound obtained can be reduced, e.g., by a boron hydride, into a compound of the formula

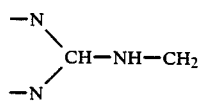

see, for example, King, *Biochemistry*, 5, 3454 (1966), and Nakaya, et al., *J. Biochem. Tokyo*, 61, 345 (1967).

In special embodiments, the process of preparing the antigens may further have the following characteristics, taken separately or in combination:

Dialdehyde is made to react with hapten and with the amine molecule, generally in aqueous solution and at a temperature of from 15° to 25°, until the end of the coupling reaction. The end of the coupling reaction is generally signaled by the appearance of coloration in the reaction solution and by stabilization of the pH. If necessary, measures are taken to prevent oxidation of the hapten, when the latter possesses an easily oxidizable group. The excess dialdehyde can be made to react with a solution of the amine molecule, to which hapten is added, or with hapten, to which the amine molecule is added, or even with a solution containing both hapten and the amine molecule.

In cases where the hapten may be an amino acid, it is preferentially made to react with an excess of dialdehyde (e.g., an excess of ten times the stoichiometric quantity), and the amine molecule is added to the product obtained. In the case of an amine molecule with highly reactive groups, this molecule is first made to react with an excess of dialdehyde. The nonreacted dialdehyde is then eliminated (e.g., by dialysis), and the product obtained is made to react with the second amine and/or guanidine reagent.

Dialdehyde is added in sufficient quantity to cause reaction of the maximum number of —NH$_2$ or guanidine groups of the macromolecule. Of course, the hapten must be present in at least equivalent molar quantities.

The dialdehyde is glutaraldehyde.

The reducing agent is a nondenaturing agent in cases where the carrier is a protein. In particular, a hydride may be used, especially a boron hydride such as sodium boron hydride.

Of course, if the hapten contains reducible groups that are reduced simultaneously with the imine, these groups may be reoxidized, if necessary, using known methods.

The invention also concerns the application of antibodies as defined above. This application consists chiefly of using known immunochemical and immunocytochemical techniques that enable one to detect and determine the quantities of the haptens in question in solutions, in deproteinized cell or tissue extracts, or in suitably fixed tissue cuttings. The localization of a neuromediator, the site of fixation of a medication, and other phenomena may also be studied.

For example, to detect and determine the quantity of a hapten in solution, the solution to be tested is placed in contact with a backing coated with an aminated molecule (e.g., polylysine). The backing may be a solid backing usable in chromatography or a backing that forms a microtitration plate dish. A dialdehyde of the formula $$O=CH-(CH_2)_{\overline{n-2}}CH=O$$

(preferentially identical to the one used to prepare the immunogen used to obtain the antibodies) is added in order to couple the hapten. Commercial aminated backings on which an excess of dialdehyde has already been fixed may also be used. These backings are placed into contact with the hapten solution. After reduction of the neoformed double bonds, as previously, the backing is brought into contact with a solution containing the marked antibodies capable of selectively identifying the hapten under study.

Next, one simply reveals the presence of the marked antibodies that may have become fixed onto the backing to discover whether the hapten was present and possibly to measure its quantity.

In the case of quantitative determinations, reduction of the double amine bonds or their analogues, after coupling or fixation of the hapten in question, is obligatory.

In the case of a qualitative test, particularly an immunocytochemical one, this reduction is generally not necessary, as is shown in the experimental portion of this application.

In other words, for immunocytochemical tests, it is generally enough to fix the tissue cuttings using the dialdehyde employed in the preparation of the immunogens used in obtaining the antibodies, and then to place the fixed tissue cuttings in contact with the marked antibodies targeted against the hapten under study. After rinsing, any fixation of the hapten onto the tissue is then revelaed.

More detailed explanations of certain specific examples will be given hereinafter in the experimental portion hereof.

The following examples illustrate the invention without limitation.

In these examples, antigens are sometimes designated by shortened formulas whose meaning is obvious for specialists. For example, in the case where the dialdehyde is glutaraldehyde, the compound of formula V may be designated using an abridged formula, e.g., where $x_2 = 0$:

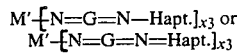

(or even by an even more schematic formula of the type M'=G=Hapt.), in which G is of course the carbon chain derived from the glutaraldehyde, following reaction with the aminated molecules, i.e., here =CH—(CH$_2$)$_3$—CH=. Similarly, the antigen of formula III will be abridged M'—[NH—G—NH—Hapt.]$_x$, in which G this time is the carbon chain derived from glutaraldehyde after reduction of imine, i.e., here —CH$_2$—(CH$_2$)$_3$—CH$_2$—, or even more simply, M'—G—Hapt.

In some cases, the abbreviation GA has been used instead of G.

EXAMPLE 1

Obtaining antibodies targetted against catecholamines

Synthesis of immunogens from dopamine (DA) and p-tyramine

Each hapten is coupled with bovine serum albumin (BSA, Sigma).

Ten mg of dopamine (Sigma) chlorhydrate are dissolved in 1 ml of distilled water. One ml of a solution containing 30 mg of BSA in 1 ml of 3M acetate buffer, pH 8, are added. After 3 minutes at ambient temperature a reddish-orange coloration appears and the pH stabilizes, marking the end of the coupling reaction. Next, 1 ml of a solution of 10 mM of sodium boron hydride (Merck) is added. The reaction mixture becomes translucent at the end of the reaction. The solution obtained is dialyzed against water for 2 days at 4° C. The insoluble substances are eliminated by centrifugation through a Millipore filter of the 0.45 micrometer type. For analysis, the conjugate obtained is lyophilized. The molar ratio of dopamine to BSA is 38.

Analogously, a conjugate of p-tyramine was prepared from 10 mg of p-tyramine chlorhydrate (Sigma). Analysis of the lyophilized conjugate shows that the molar ratio of tyramine to BSA is 40.

Immunization

Rabbits are immunized with immunogens previously obtained using the method described by Vaitukaitis, J. L., et al., *J. Clin. Endocr.*, 33, pp. 988–991 (1971).

For each immunogen, 500 micrograms of immunogen emulsified in 500 microliters of a solution of NaCl 0.15M and 750 microliters of Freund complete adjuvant are administered subcutaneously to two rabbits. A booster shot is given every month for 4 months. Between two boosters, an intramuscular injection is given.

Synthesis of radioactive ligands

Dopamine (DA) and N-α-acetyl-L-lysine N-methylamide (abbreviated ALM and commercialized by Sigma) are coupled using glutaraldehyde under the same conditions as those described above for obtaining the immunogen. For this purpose, 500 microliters of a solution of ALM, 0.1M, pH 8, are mixed with 100 microliters of a 3M acetate buffer and 40 microliters of tritiated DA. 100 ml of a 5% glutaraldehyde solution are then added. After 3 minutes, sodium boron hydride is added to saturation for 30 minutes. The reaction mixture is diluted with 1 ml of phosphate buffer and placed on a Sephadex SP C25 column. It is eluted with a gradient of NaCl, 10 mM-0.8M in a 10 mM phosphate buffer at pH 6.2.

Analogously, the conjugate of tritiated tyramine (TA) and N-α-acetyl-L-lysine N-methylamide is prepared.

In the same way one also prepares conjugates of N-α-acetyl-L-lysine N-methylamide and the following nonradioactive compounds: dopamine (DA), tyramine (TA), noradrenalin (NA), octopamine (OA), and L-DOPA.

Incubation

The reaction of the ligands thus prepared with the antibodies obtained above is studied using the method of equilibrium dialysis according to the techniques described by Cailla, H. L., et al., *Anal. Biochem.* 56, pp. 383–393 (1973).

The dialysis cells are separated by large-pore cellulose membranes (Sartorius S. M. 11 533 or Schleicher and Schull membrane RC 50). The antibody solution is placed on one side of the membrane. Each conjugate of catecholamine is mixed with an equal volume of radioactive ligand before being placed on the other side of the membrane. The incubation solution of each antiserum is a citrate buffer 0.1M (pH 6.2) containing 1 mg/ml of bovine serum albumin (BSA) and 10 mM of sodium azide (N$_3$Na). The final volume is 2×150 microliters. This is left to incubate at 4° C. for 20 hours. Next the beta radioactivity in a sample of 100 microliters taken from each side of the membrane is counted.

RESULTS

In order to determine, during immunization, the titer of the antibodies and their cross-reactivity, the competition method was used.

Titers of anti-DA and anti-TA antibodies

The synthesized radioactive ligands above are designated ($^3$H) DA-G-ALM and ($^3$H) TA-G-ALM respectively.

These radioactive ligands made it possible to follow the development of immunization with a dilution of the antibodies to 1/500. The antibody titer had already increased after 4 injections (2 boosters and 2 intramuscular).

For the anti-TA antibodies, the titer rose sharply after the fifth injection. For these latter antibodies, it was possible to use a dilution of 1/2000.

Specificity of the antibodies and their affinity (a) Specificity of the anti-DA antibodies In order to perform a quantitative study, we studied the displacement of ($^3$H) DA-G-ALM by noncoupled DA and by the various derivatives of the catecholamines mentioned above. The best displacement was observed with DA-b-ALM between $10^{-9}$ and $10^{-7}$M, which corresponds to a rather high affinity constant ($KA = 6.7 \times 10^7$ l.mol.$^{-1}$).

Unmodified dopamine is not capable of displacing the ($^3$H) DA-G-ALM, even at a concentration of $10^{-6}$M ($KA = 6.7 \times 10^3$ l.mol.$^{-1}$).

The derivatives of other catecholamines conjugated with ALM have a slight immunoreactivity, much lower, however, than that of DA-G-ALM. The most reactive compound is NA-G-ALM ($KA = 5 \times 10^5$ l.mol.$^{-1}$). Thus, the reactivity of the latter compound is 53 times lower than that of DA-G-ALM.

For the other derivatives, the cross-reactivity is even lower. The following affinities were found:

| Conjugates | KA l. mol.$^{-1}$ |
|---|---|
| L-DOPA—G—ALM | $3.8 \times 10^5$ |
| OA—G—ALM | $5 \times 10^4$ |
| TA—G—ALM | $3.1 \times 10^4$ |

No displacement was observed for the conjugates DA-G-ALM and TA-G-ALM.

(b) Specificity of anti-TA antibodies

The displacement of ($^3$H)-TA-G-ALM by various conjugated molecules belonging to the catecholamine family was studied in the same way. In this situation, the best displacement was observed with:

TA-G-ALM ($KA = 7 \times 10^7$ l.mol.$^{-1}$).

The uncoupled TA ($KA = 10^4$ l.mol.$^{-1}$) was incapable of displacing the unconjugated ($^3$H)-TA-G-ALM.

The following conjugates showed a slight immunoreactivity:

| Conjugates | KA l. mol.$^{-1}$ |
|---|---|
| OA—G—ALM | $5.9 \times 10^5$ |
| L-DOPA—G—ALM | $3.3 \times 10^5$ |

No displacement was observed with conjugates DA-G-ALM ($KA = 2.6 \times 10^4$ l.mol.$^{-1}$) and NA-G-ALM ($KA = 1.4 \times 10^4$ l.mol.$^{-1}$).

Physiochemical characterization of the two antiserums (i) Dissociation constants (kd)

Anti-DA: $Kd = 1.48 \times 10^{-8}$M

Anti-TA: $Kd = 1.43 \times 10^{-8}$M

These constants were obtained with the best ligand (DA-G-ALM for the anti-DA antibodies; TA-G-ALM for the anti-TA antibodies).

(ii) It was possible to compute the affinity constant (KA) for each compound with the best ligand. These values, which were indicated above, show the very high affinity of the antibodies.

(iii) The free bond energy (Fo= −RT Log KA) was computed at 5° C. The results are the following:

Anti-DA: $\Delta Fo = -9.91$ Kcal/mol.

Anti-TA: $\Delta Fo = -9.93$ Kcal/mol.

The heterogeniety index was determined using Sips' equation:

$$\log r/2 - r = a(\log KA + \log c)$$

in which $r = B/T$; KA = affinity constant; a = heterogeneity index.

The results are as follows:

Anti-DA: $a = 0.63$

Anti-TA: $a = 0.56$

Comparison of the affinity of the antibodies for nonsaturated derivatives of formula V The anti-DA and anti-TA antibodies recognize the nonsaturated derivatives ($^3$H) DA=G=ALM and ($^3$H) TA=G=ALM obtained through coupling with glutaraldehyde without later reduction of the imine groups. However, the antibody dilutions used were much weaker than those used with the saturated conjugates (1/200).

The study showed that the curves of displacement of ($^3$H) DA=G=ALM by DA=G=ALM and of ($^3$H) TA=G=ALM by TA=G=ALM are superimposed. Self-displacement for each molecule lies between $10^{-8}$ and $10^{-6}$M.

The constants of affinity were computed for the nonsaturated ligands. The results are as follows:

Anti-DA: $KA = 9.1 \times 10^6$ l.mol.$^{-1}$

Anti-TA: $KA = 6.3 \times 10^6$ l.mol.$^{-1}$

The antibodies obtained therefore make it possible to identify unsaturated conjugates. It is thus unnecessary, after fixation of the antigen, to reduce the double bond in order to study the antigen using the antibodies of the invention.

It emerges from the preceding study of two antibodies targeted against the catecholamines DA and TA that a slight difference in the structure of the hapten (presence of an additional hydroxyl group in dopamine) can induce a highly specific immune response for the two different conjugates. The anti-DA antibodies do not recognize the conjugate TA-G-ALM, while the anti-TA antibodies have no affinity for the conjugate DA-G-ALM.

It is therefore apparent that the anti-DA and anti-TA antibodies can be used in the immunocytochemical study of dopamine and p-tyramine.

Anti-NA (NA = norepinephrine) and an anti-OA (OA = octopamine) antibodies were prepared in a manner analogous to that described above.

Anti-NA antibodies

Studies of specificity showed that the best displacement was obtained with the conjugate NA-G-ALM; $KA = 3.8 \times 10^7$ l.mole$^{-1}$.

Nonconjugated NA caused no displacement.

Anti-OA antibodies

The characteristics of the anti-OA antibodies obtained are: $Ka = 5 \times 10^6$ l.mole$^{-1}$.

EXAMPLE 2

Obtaining antibodies targeted against aminated acids

The case of gamma-aminobutyric acid is described below as an example.

Synthesis of immunogenic conjugates

Ten mg of gamma-aminobutyric acid (GABA) and 2 microliters of ($^3$H) GABA are mixed in 1 ml of distilled water with 1 ml of 3M acetate buffer at pH 7.8 containing either 30 mg of bovine serum albumin (BSA, Sigma) or 30 mg of bovine hemoglobin (Hb, Sigma) or 30 mg of poly-L-lysine (PL, Peninsula). One ml of a 5% solution of glutaraldehyde is added. The reaction lasts 3 minutes at ambient temperature. Completion of the reaction is signaled by the appearance of a yellow-orange color and by stabilization of the pH around 7. One ml of a 10 mM solution of sodium boron hydride (Merck) is then added. After reduction, the reaction mixture becomes translucent. The solution is then dialyzed at 4° C. and the precipitate eliminated by centrifugation, as described in example 1.

The beta radioactivity for a given weight of lyophilized conjugate is counted.

From this, it can be deduced that the molar proportions of the conjugates are as follows:
GABA/BSA: 21
GABA/Hb: 50
GABA/PL: 34

Synthesis of radioactive ligands

In a manner analogous to that described in example 1, the amine group of the GABA is coupled with an aminated molecule, which here is tripeptide proline-phenylalanine-lysine (PPL, Bachem), using glutaraldehyde.

The coupling reaction between tritiated GABA, designated by ($^3$H) GABA (Amersham) and PPL is performed under the same conditions as the coupling of the immunogens. 500 microliters of PPL, 0.1M, pH 8, are mixed with 100 microliters of 3M acetate buffer and 40 microliters of ($^3$H) GABA. 100 microliters of a 5% solution of glutaraldehyde are added. After 3 minutes, sodium boron hydride is added and left to act for 30 minutes. The mixture is diluted with 1 ml of phosphate buffer before being placed on a column of quaternary ammonium ethyl sephadex (QAE Sephadex) (Pharmacia). Elution is done using a sodium chloride gradient as described above.

Synthesis of conjugates of various amino acids

In an analogous manner, using glutaraldehyde, PPL is coupled with the following amino acids: GABA, glycine, beta-alanine, glutamate, aspartate, taurine. Following chromatography on QAE Sephadex, the concentration of each derivative is computed by spectral analysis and counting of beta-radioactivity. The molar proportion of the amino acid and the carrier (PPL) is computed and the concentrations of the various conjugates determined.

In the case of the immunogen coupled with taurine, the sulfonate group of the taurine is reduced with the imine but is easily reoxidized with oxygenated water (H2O2) in a 0.1M acetic milieu.

Immunization

Rabbits are immunized as described in example 1. For the first injection, the conjugate GABA-GA-BSA is used as the immunogen; for the second, the conjugate GABA-GA-Hb; for the third, GABA-GA-PL; for the fourth, GABA-GA-BSA; and so on.

Immunization is carried out over a period of four months.

Incubation (radioimmunoassays)

As in example 1, the method of equilibrium dialysis was used.

Immunocytochemical studies

Rat brains were fixed by perfusion with a 5% solution of glutaraldehyde in a cacodylate buffer, 0.1M, pH 7.5. The brain was cut in slices approximately 4 mm thick and then fixed again for 1.5-2 hours using the same fixative.

Sections of 50 micrometers were incubated with GABA antiserum diluted to 1/1,500. This antiserum was visualized using the peroxidase-antiperoxidase method, with diaminobenzidine as the chromogen. See Sternberger, L. A., Immunochemistry (1979) 2nd ed. (John Wiley and Sons, New York) and Buijs, R. M., Immunocytochemistry and its Application in Brain Research, Van Leeuwen, F. W., Swaab, D. F., and Buijs, R. M., eds. (Embo, Amsterdam), pp. 49–55.

RESULTS

Titer of GABA antiserum

The maximum titer is obtained after the ninth immunization, i.e., at the end of the fourth month.

Specificity of the anti-GABA antiserum

Studies of specificity were conducted using the method of equilibrium dialysis, by competition of the tracer ($^3$H) GABA-GA-PPL and the various conjugated analogues GABA-GA-PPL, glycine-GA-PPL, etc.

Unmodified GABA was incapable of displacing the radioactive ligand even at a concentration of $10^{-5}$M.

The conjugates were very badly identified by the antibody. The most immunoreactive compounds were the conjugates of beta-alanine and glycine, which had respective cross-reactivities 175 and 795 times less than that of the GABA-GA-PPL conjugate.

No reactivity was observed with the conjugates of aspartate and glutamate at concentrations between $10^{-9}$M and $10^{-8}$M. For the taurine conjugate, reactivity is on the same order or magnitude as with the conjugate of aspartate or glutamate.

It should be noted that the solid phase purification of the antiserums obtained in this example is not necessary.

Immunocytochemical results

Extinction of coloration following mixture of the pure serum with an immunogenic solution is observed. A very great reduction in coloration was noted following absorption with a $10^{-3}$M solution of free GABA.

No qualitative or quantitative difference in coloration appeared after the serum was mixed with the following conjugates: glutamate-GA-BSA, aspartate-GA-BSA, taurine-GA-BSA, glycine-GA-BSA, and beta-alanine-GA-BSa.

Using the anti-GABA antibodies on cuttings fixed with glutaraldehyde, an intense coloration in the fibers and cells of several regions of the brain was obtained. Several reactive cell bodies were visible even without using colchicine. The fibers containing GABA were found in practically all regions of the brain, including all layers of the cerebral cortex, with several sites in cell bodies, probably interneurons.

These results confirm those that have been observed by other means. In particular, the presence of GABA in the hippocampus must be pointed out, especially in the innervation of granular and pyramidal cells, and in Golgi cells and the star-shaped cells of the cerebellum.

Conclusions

It is therefore possible to obtain antibodies against small linear molecules such as GABA.

The procedure described here makes it possible to produce specific antibodies that are very sensitive.

The immunogens obtained following coupling by glutaraldehyde, and without reduction of the double imine bonds, produce antibodies that are nonspecifically targeted against said imines, and it is necessary to carry out several solid phase purifications in order to eliminate these parasite antibodies. On this subject see Storm-Mathisen, et al., *Nature* (London, 1983) 301, pp. 517-20.

Reduction of the imines formed in the reaction with glutaraldehyde thus appears to be a decisive step in obtaining highly specific antibodies.

The tests of specificity made it possible to compute the dissociation constant and the standard free energy of the antibodies prepared.

These constants are as follows:

| Antigen | Kd | ΔFo |
|---|---|---|
| GABA—GA—lysine | $2 \times 10^{-8}$ M | $-9.8$ Kcal/mol |

The immunocytochemical tests performed with anti-GABA antibodies acting on the brain cuttings enabled us to confirm earlier discoveries indicating that GABA neurons innerve practically all parts of the central nervous system.

Antibodies targeted against the following amino acids were prepared in an analogous fashion.
taurine
aspartic acid
glutamic acid For the anti-taurine antibodies, it was found that $Kd = 5 \times 10^{-8}$ M.

EXAMPLE 3

Preparation of antibodies targeted against indolamines

Antibodies targeted against each of the following various indolamines were prepared in the same way.

Synthesis of immunogens

Proceeding as in the foregoing examples, we prepared the following immunogens:
BSA-G-W
BSA-G-HW
BSA-G-MW
BSA-G-T
BSA-G-MT
BSA-G-HT
as well as the same immunogens with HSA instead of BSA.

Abbreviations

BSA: bovine serum albumin
HSA: human serum albumin
W: L-tryptophane
HW: 5-hydroxytryptophane
MW: 5-methoxytryptophane
T: tryptamine
MT: 5-methoxytryptamine
HT: 5-hydroxytryptamine (or serotonin)

Synthesis of ligands

As in the preceding examples, the following conjugated ligands were prepared:

W-G-PL; HW-G-PL; MW-G-PL; HT-G-PL; T-G-PL

For purposes of comparison, the intermediate nonreduced conjugates were studied. These were:

W=G=PL; HW=G=PL; MW=G=PL; HT=G=PL; MT=G=PL; T=G=PL

Abbreviation

PL signifies poly-L-lysine (M.W. 60,000)

Immunization and obtainment of antibodies

Work proceeded as in the previous examples.

Study of the affinity and specificity of the antibodies

This study was performed using an ELISA test (Enzyme-linked immunosorbent assay). The plates were coated with a solution of BSA-G-indolamine conjugate and then saturated with bovine serum. they were then placed in contact with the antibody solution under study, and then with anti-(rabbit gammaglobulin) goat antibodies conjugated with peroxidate of horseradish. Fixation of the antibodies was revealed by measuring optic density with a solution of o-phenylenediamine containing oxygenated water.

RESULTS

Anti-W antibodies

Displacement curves obtained using the competition method show that the best displacement could be observed with W-G-PL. Self-displacement lay between $10^{-9}$M and $10^{-7}$M. Nonconjugated tryptophane was only weakly identified. The nonreduced conjugate W=G=PL was 444 times less reactive than W-G-PL.

Anti-HW antibodies

The best displacement was obtained with HW-G-PL (5 times less with HW=G=PL).

Anti-HT antibodies

The best displacement was obtained with HT-G-PL. The nonconjugated hapten was only weakly identified.

Anti-MW antibodies

Best displacement with MW-G-PL.

Immunoreactivity of MW=G=PL was 13 times lower.

Anti-MT antibodies

Best displacement with MT-G-PL (12 times less with MT=G=PL).

Specificity tests made is possible to compute constants Kd. These are indicated in the following table:

| Haptens | Dissociation constant Kd (moles/liter) |
|---|---|
| 5-methoxytryptophane | $1.40 - 10^9$ |
| Tryptophane | $7.2 - 10^{-9}$ |
| 5-hydroxytryptophane | $1.35 - 10^{-8}$ |
| 5-methoxytryptamine | $2.2 - 10^{-8}$ |
| Tryptamine | $2.4 - 10^{-9}$ |
| Serotonin | $3.0 - 10^{-9}$ |

EXAMPLE 4

Preparation of anti-tetrodotoxin antibody

It will be recalled the tetrodotoxin (abbreviated TTX) is described by the following formula:

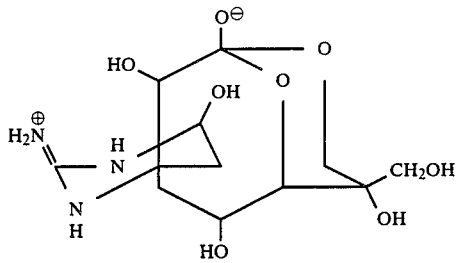

Synthesis of the immunogen

This was done through two processes:

(A)—Prior activation of the carrier protein by glutaraldehyde (G)

1. Activation of the carrier protein by glutaraldehyde: To 30 mg of human serum albumin (HSA) diluted in 1,500 ml of 1M sodium acetate solution, pH=8, 3 ml of a 1M glutaraldehyde solution (Merck) are added very quickly. The mixture is dialyzed against water at 4° C. for 2 days to eliminate the nonfixed glutaraldehyde.

The coupling produces HSA=G.

2. Five mg of the glutaraldehyde-activated protein are taken following lyophilization in a 0.75M acetate solution, pH=7.5, and mixed with 300 microliters of a 1 mg/ml TTX solution in water. The mixture is left at ambient temperature for 30 minutes. The unreduced conjugate HSA=G=TTX is obtained.

The pH is brought back to 6 by addition of 500 microliters of 0.2M citrate buffer, pH=4.8.

3. The neoformed imine groups are reduced by addition of a 0.1M solution of sodium boron hydride.

4. The reduced conjugate HSA-G-TTX is dialyzed for a day and a half against water at 4° C.

5. A sample of each dialyzate (n=4) is taken for purposes of testing the concentration of TTX released in the course of the dialysis (nonconjugated TTX) using a bio-assay (the technique of which is set forth below). The biological activity of each immunogen is tested with this assay.

The molar ratio of TTX and albumin in the conjugate obtained was between 3 and 4.

(B)—Prior activation of TTX with glutaraldehyde

1. One ml of a $10^{-3}$M solution of TTX in a 2M sodium acetate medium, pH=7.6, is activated with 50 microliters of 0.1M glutaraldehyde (G) (a G concentration of $5\times10^{-3}$M). The final pH of the mixture is 7.2. The coupling produces G=TTX.

2. After a half hour, 500 microliters of a 0.75M sodium acetate solution containing 8 mg of serum albumin (HSA) are added. The mixture is left thus for a half hour at the temperature of the laboratory. The TTX=G becomes fixed on the free amine groups of the protein to produce the conjugate HSA=G=TTX.

3. The neoformed imine double bonds are reduced with the addition of 500 microliters of 0.2M citrate buffer, pH=4.8, containing sodium boron hydride. The conjugate HSA-G-TTX is obtained.

4. The conjugate is dialyzed against water at 4° C. for 3 hours to remove excess nonconjugated TTX or the easily dialyzable TTX-G-TTX dimers.

The concentration of fixed TTX is determined by bio-assay, by measuring the activity of the TTX on an aliquot at each step of the hemisynthesis of the immunogenic conjugate.

The molar ratio of TTX to albumin in the conjugate obtained was between 10 and 15.

Immunization

Immunization was performed as in the preceding examples.

Study of the specificity of anti-tetrodotoxin antibodies using ELISA method

This test comprises 4 successive steps:

1. Adsorption of the antigen (or immunogen) on a microtitration plate (Nunc).

2. Antigen-antibody reaction (I complexes)

3. Formation of II complexes through fixation of anti-IgG rabbit antibodies coupled with peroxidase onto I complexes.

4. Visualization of II complexes by action of peroxidase on a chromogenic substrate: orthophenylenediamine (OPD).

First step: coating of the plate.

TTX-G-HSA conjugate (and HSA-G for comparison) is diluted in a carbonate buffer, $5\times10^{-2}$M, pH=7.5. The dilution used in this system is given by the best signal/noise ratio. In this case, it was 7.5 μg/ml. 200 μl of each solution are deposited in the dishes and left for 16 hours at 4° C. After this time, each dish is emptied and rinsed three times with buffer A (phosphate buffer, $10^{-2}$M, NaCl, 0.15M, pH=7.4).

Second step: application of the primary antibody (anti-TTX antibody).

Beforehand, the serum is absorbed on proteins treated with glutaraldehyde and reduced for 16 hours at 4° C.

The immunocomplexes obtained through identification of the anti-protein-carrier immunoglobulins are eliminated by immunoprecipitation. The prepurified serum is diluted to 1/20,000 in buffer A, to which 1% bull serum is added. 200 microliters are placed in each dish containing either immunogen TTX-G-HSA or G-HSA. An incubation period of 2 hours allows the antigen-antibody reaction to become optimal. It is followed by 3 rinsings with buffer A.

Third step: application of anti-IgG antibodies marked with peroxidase (secondary antibodies).

The anti-rabbit-IgGs are obtained from goat immune serums. They are diluted at 1/10,000 in buffer A containing 1% bull serum. The period of incubation is 1 hour, at 37° C. This is followed by 3 washings with buffer A.

Fourth step: application of OPD.

200 microliters of a solution containing oxygenated water (H202) and OPD are placed in each dish. The solution is prepared extemporaneously in a solution of citrate-phosphate buffer, 0.1M, pH=5, in order to obtain a final concentration of 0.5 mg/ml of OPD and 0.025% $H_2O_2$. The reaction is allowed to develop in darkness for 10 minutes and is then halted by the addition of 50 microliters of 4N sulfuric acid in each dish.

Absorbance is read at 492 nm on the spectrophotometer.

The values observed are corrected by substracting the experimental values read in the control dishes containing G-HSA.

RESULTS

Specificity of anti-TTX antibodies

One hour of competition between the immunogen TTX-G-HSA in the dish and the pre-incubated conjugate with the purified antibody at 37° C. produces displacement curves showing that self-displacement occurs between $10^{-10}$ and $10^{-7}$ for the immunserums obtained. This result indicates a good affinity of the anitbody sites obtained for the TTX-G- hapten group. Indeed, the nonconjugated TTX is less well identified. This result underlines the importance of the glutaraldehyde residue reduced in the immunoidentification.

The immunogen TTX-G-HSA, synthesized using method A, retains the property of blocking the potential for action. This effect is apparently comparable to that of the initial TTX. Dialysis of the immunogen makes it possible to eliminate nearly all trace of free TTX. Under these conditions, the blocking effect of the immunogen is approximately 50 times stronger than the toxic effect of the free TTX in the third dialyzate of the TTX-G-HSA immunogen. The immunogen synthesized according to method B is even more active, with the TTX-G-HSA (after dialysis) being approximately 500 times more active than the free TTX found in the dialyzate.

Technique of determining the quantity of TTX by blocking conduction of nervous influx (Technique of determining TTX by bioassay.)

The effect in which conduction of the nervous influx is blocked as a function of tetrodotoxin (TTX) concentration was studied on the sciatic nerve of the frog. The technique used is similar to that described by Seeman et coll. (Canad. *J. Physiol. Pharmacol.*, 50, 1181-1192) and Levinson (*Phil. Trans. R. Soc. London* B, 270, 337-348). The sciatic nerve is removed and stripped. This technique permits direct and rapid access of the toxin to the Ranvier nodes.

The stripped nerve is placed a five-compartment plexiglass chamber. The two compartments on each side of the chamber contain platinum electrodes for stimulation and recording, respectively, while the central compartment is used to apply the toxin. The compartments are electrically insulated from each other. They are filled with Ringer solution for frogs. The chamber is kept at a constant temperature of 20° C.

The nerve is stimulated every two seconds with a neurostimulator. The action potentials are recorded.

The dose-response curve is obtained by depicting the percentage of the amplitudes of the nonblocked action potentials of the nerve as a function of TTX concentration, against the amplitude of the action potential of the same nerve in the Ringer solution. The concentration of tetrodotoxin that induces 50% blockage of the action potential amplitude ($A_{50}$) lies between 15 and $30 \times 10^{-9}$M. The precision of the method is on the order of ± 5%.

The composition per liter of the Ringer solution used is as follows: NaCl 110 mM; KCl 2.5 mM; $CaCl_2$ 2 mM; Tris 5 mM, pH=7.3.

I claim:

1. Antibodies capable of specifically identifying hapten groups having the formula $$-NH-(CH_2)_n-NH-Hapt.$$

wherein n is a whole number ranging from 4 to 6, and

Hapt. is the residue of a hapten molecule having the formula Hapt.—$NH_2$, wherein —$NH_2$ is a primary amine group or having the formula Hapt.=NH, wherein =NH is an imine or a guanidino group, said hapten being dihydroxyphenylalanine, dopamine, norepinephrine, tyramine, octopamine, an indolamine, glutamic acid, aspartic acid, taurine, gamma-aminobutyric acid, phenylalanine, saxitoxin or tetrodotoxin.

2. The antibodies of claim 1 wherein said hapten is selected from the group consisting of phenylalanine, dihydroxyphenylalanine, dopamine and norepinephrine.

3. The antibodies of claim 1 wherein said hapten is selected from the group consisting of tyramine and octopamine.

4. The antibodies of claim 1 wherein said hapten is selected from the group consisting of tetrodotoxin and saxitoxin.

5. The antibodies of claim 1 wherein said hapten is tetrodotoxin.

6. The antibodies of claim 1 marked with a radioactive, fluorescent or enzyme tracer.

7. The antibodies of claim 1 fixed upon a backing.

8. The antibodies of claim 1 wherein said hapten is an indolamine.

9. The antibodies of claim 8 wherein said indolamine is selected from the group consisting of serotonin, 5-hydroxytryptophane, 5-methoxytryptophane, δ-methoxytryptamine, tryptophane and tryptamine.

10. A process for detecting or determining the quantity of a hapten in solution or on a cellular tissue cutting by using the antibodies of claim 1 which are capable of selectively identifying said hapten, wherein said hapten is fixed (i) either by placing a backing, coated with an aminated molecule, in contact with the solution being tested, said solution containing a dialdehyde or (ii) by placing the said tissue cutting in contact with a dialdehyde solution, said dialdehyde being identical to that employed in the preparation of an immunogen used to obtain the said antibodies, placing said fixed tissue or backing in contact with a solution containing the said antibodies, in the form of marked antibodies, and revealing the presence of or measuring the amount of marked antibodies which become bound to the backing or tissue cutting in relation to the quantity of hapten.

11. The process of claim 10 wherein the imine bonds, formed by (i) either placing a backing coated with an aminated molecule, in contact with the solution being tested, said solution containing a dialdehyde or (ii) by placing the said tissue cutting in contact with a dialdehyde solution, are reduced.

12. A process for preparing the antibodies of claim 1 comprising
(a) immunizing an animal through the repeated administration of at least one immunogen of the formula $$[M]\!-\!\![NH\!-\!(CH_2)_n\!NH\!-\!Hapt.]_x$$

wherein

M is the residue of an aminated macromolecule of the formula $(NH)_{\overline{x_2}}[M]\!-\!(NH_2)_{x_1}$, wherein $-NH_2$ is a primary amine group and $-NH$ is an imine of a guanidino group, Hapt. is the residue of a hapten molecule having a formula Hapt.—$NH_2$, wherein —$NH_2$ is a primary amine group or having the formula Hapt.=NH, wherein =NH is an amine of a guanidino group, said hapten being as defined in claim 1, n is a whole number ranging from 4 to 6, $x_1$ is a number equal to or greater than 1 and is at most equal to the number of primary amine groups, —$NH_2$, carried by said aminated macromolecule, $x_2$ is 0 or a number at most equal to the number of guanidino groups carried by said aminated macromolecule, and x equals $x_1 + x_2$, (b) collecting the resulting seral antibodies from said immunized animal.

13. The process of claim 12 comprising fixing said seral antibodies upon a backing or reacting said seral antibodies with a radioactive, fluorescent or enzyme marker.

14. Antigens comprising a hapten having a primary amine group or a guanidino group, said hapten being linked to an aminated molecule by a coupling agent, said antigens having the formula $$[M']\!-\!\![NH\!-\!(CH_2)_n\!NH\!-\!Hapt.]_x$$

wherein

M' is the residue of an aminated molecule of the formula $$(HN)_{\overline{x_2}}[M']\!-\!NH_2)_{x_3},$$

Hapt. is the residue of a hapten molecule having the formula Hapt.—$NH_2$, wherein —$NH_2$ is a primary amine group or having the formula Hapt.=NH, wherein =NH is an imine of a guanidino group, said hapten being as defined in claim 1, n is a whole number ranging from 4 to 6, $x_3$ is 0 or a number at most equal to the number of primary amine groups, —$NH_2$, carried by said aminated molecule, $x_2$ is 0 or a number at most equal to the number of guanidino groups carried by said aminated molecule, and x equals $x_3 + x_2$ and is greater than zero.

15. The antigens of claim 14 wherein said aminated molecule carries at least one lysine unit having a free $\epsilon$-$NH_2$ group.

16. The antigens of claim 14 wherein said aminated molecule is an antigenic macromolecule.

17. The antigens of claim 14 wherein said aminated molecule is a protein, a protein fragment, a synthetic polypeptide or a semi-synthetic polypeptide.

* * * * *